United States Patent
Daniels

(10) Patent No.: US 10,231,633 B2
(45) Date of Patent: Mar. 19, 2019

(54) MULTI-PROTOCOL HEART RATE MONITOR

(71) Applicant: Doug Daniels, Boulder, CO (US)

(72) Inventor: Doug M. Daniels, Lone Tree, CO (US)

(*) Notice: Subject to any disclaimer, the term of this patent is extended or adjusted under 35 U.S.C. 154(b) by 337 days.

(21) Appl. No.: 15/264,173

(22) Filed: Sep. 13, 2016

(65) Prior Publication Data

US 2017/0071480 A1    Mar. 16, 2017

Related U.S. Application Data

(60) Provisional application No. 62/217,925, filed on Sep. 13, 2015.

(51) Int. Cl.
| | |
|---|---|
| *A61B 5/04* | (2006.01) |
| *A61B 5/0245* | (2006.01) |
| *A61B 5/00* | (2006.01) |
| *A61B 5/0402* | (2006.01) |
| *A61B 5/024* | (2006.01) |

(52) U.S. Cl.
CPC .......... *A61B 5/0245* (2013.01); *A61B 5/0004* (2013.01); *A61B 5/0015* (2013.01); *A61B 5/02438* (2013.01); *A61B 5/0402* (2013.01); *A61B 5/6804* (2013.01); *A61B 5/7278* (2013.01)

(58) Field of Classification Search
CPC ... A61B 5/0245; A61B 5/0402; A61B 5/0015; A61B 5/7278; A61B 5/6804; A61B 5/02438; A61B 5/0004
See application file for complete search history.

(56) References Cited

U.S. PATENT DOCUMENTS

| | | | |
|---|---|---|---|
| 7,698,101 | B2 | 4/2010 | Alten et al. |
| 7,813,715 | B2 | 10/2010 | McKillop et al. |
| 7,927,253 | B2 | 4/2011 | Vincent et al. |
| 8,054,176 | B2 | 11/2011 | Karjalainen |
| 2006/0041200 | A1 | 2/2006 | Dotter et al. |
| 2006/0135863 | A1 | 6/2006 | Birnbaum et al. |
| 2007/0021269 | A1 | 1/2007 | Shum |
| 2007/0078324 | A1 | 4/2007 | Wijisiriwardana |
| 2007/0127187 | A1 | 6/2007 | DeFusco et al. |
| 2008/0147926 | A1 | 6/2008 | Chen |
| 2008/0287769 | A1 | 11/2008 | Kurzweil et al. |
| 2010/0203829 | A1 | 8/2010 | Granqvist et al. |
| 2010/0210975 | A1 | 8/2010 | Anthony et al. |
| 2010/0292599 | A1 | 11/2010 | Oleson et al. |
| 2011/0255454 | A1 | 10/2011 | Hauser et al. |

*Primary Examiner* — Mallika D Fairchild
(74) *Attorney, Agent, or Firm* — Duft & Bornsen, PC

(57) ABSTRACT

Embodiments described herein provide for monitoring a user's heart rate. One embodiment comprises a heart rate monitor that includes a pair of contacts that are configured to electrically couple to one of a pair of sensors in a garment worn by a user. The monitor detects a change in impedance across the contacts, and responsive to the impedance being below a threshold, the monitor senses a cardiac electrical activity of the user utilizing the pair of sensors. The monitor calculates a heart rate of the user based on the cardiac electrical activity, determines if the heart rate is within a range of heart rate values, and responsive to the heart rate being within the range of heart rate values, the monitor simultaneously transmits the heart rate utilizing different protocols to at least one external device.

23 Claims, 4 Drawing Sheets

1

MULTI-PROTOCOL HEART RATE MONITOR

RELATED APPLICATIONS

This document claims priority to U.S. Provisional Patent Application No. 62/217,925 (filed on Sep. 13, 2015) entitled "MULTI-MODE HEART RATE TRANSMITTER", which is hereby incorporated by reference.

FIELD

This disclosure relates to the field of heart rate monitors, and in particular, to heart rate monitors that utilize multiple radios.

BACKGROUND

Heart rate monitors are often used by people that want to track and/or record their heart rate during exercise. Since heart rate during exercise is reasonably correlated with the effort put forth by the person, the heart rate of the person can be used as an indicator of the intensity of the exercise. Typically, the heart rate of the person can be segmented into different zones or ranges, with variations in the effort of exercise being used to achieve a target heart rate in one of the zones for training purposes.

Heart rate monitors are often electrically connected to a strap, which is worn by the person during exercise. The strap includes electrical pads which contact the chest of the person and conduct electrical pulses from the person's heart. Heart rate monitors amplify the electrical signals and transmit the heart rate of the person to an external device for display and/or monitoring. Some examples of an external device which may be used to display and/or monitor the heart rate of the person includes cycling computers, exercise watches, exercise equipment at a gym or at home, etc.

Over time, different heart monitor manufacturers have implemented different wireless interfaces for providing heart rate information to external devices. Some interfaces are simple analog signals, while other interfaces utilize digital protocols to provide the information. The different wireless interfaces have varying support for user-equipment, such as exercise equipment, watches, cycling head units, etc. Thus it is often the case that the use of a heart rate monitor supporting a specific wireless interface is not compatible with the external devices that are in use by the person wearing the heart rate monitor. The result is inoperability and user confusion regarding if an external device will operate with a particular heart rate monitor that is in use. Further, the heart rate strap can be uncomfortable to wear or may slide out of position during exercise. The result of the latter is the loss of connectivity to the skin, with a subsequent loss of heart rate data from the heart rate monitor.

SUMMARY

Embodiments described herein provide for monitoring a user's heart rate, and subsequently transmitting it with a plurality of RF transmitters that utilize different protocols to allow for a wider interoperability across a range of external devices.

One embodiment comprises a heart rate monitor that includes a pair of contacts that are configured to electrically couple to one of a pair of sensors in a garment. The heart rate monitor further includes a processor, control circuitry, and a plurality of Radio Frequency (RF) transmitters that transmit information utilizing different protocols. The control circuitry detects a change in impedance across the contacts, and responsive to the impedance being below a threshold, the control circuitry wakes up the processor from a sleep mode, and senses a cardiac electrical activity of the user utilizing the pair of sensors. The processor calculates a heart rate of the user based on the cardiac electrical activity, determines if the heart rate is within a range of heart rate values, and responsive to the heart rate being within the range of heart rate values, the processor powers up the RF transmitters, and directs the RF transmitters to simultaneously transmit the heart rate utilizing the different protocols to at least one external device.

In an embodiment, the processor powers down the RF transmitters and enters the sleep mode in response to the heart rate being outside of the range of heart rate values.

In an embodiment, the processor powers down RF transmitters that are transmitting the heart rate utilizing one of the protocols in response to determining that an acknowledgement (ACK) response required by one of the protocols has not been received from at least one external device.

In an embodiment, the processor powers down the RF transmitters that are not transmitting the heart rate utilizing one of the protocols in response to determining that an ACK response has been received from the at least one external device for the protocol.

In an embodiment, the heart rate monitor further includes the garment worn by the user.

In an embodiment, the garment comprises one of a sports bra, a tank top, and a bra.

In an embodiment, at least one of the RF transmitters utilizes a 5.3 kilohertz (kHz) analog signal as one of the protocols.

In an embodiment, at least one of the RF transmitters utilizes Bluetooth Low Energy (BLE) as one of the protocols.

In an embodiment, at least one of the RF transmitters utilizes ANT+ as one of the protocols.

In an embodiment, the heart rate monitor further includes a memory. The processor stores a record of the heart rate over time in the memory, identifies one of the external device that is capable of receiving the record, and transfers the record to the identified external device utilizing at least one of the RF transmitters.

Another embodiment comprises a method operable by a heart rate monitor. The method comprises detecting, by control circuitry of the heart rate monitor, a change in impedance across a pair of contacts of the heart rate monitor that are each electrically coupled to one of a pair of sensors in a garment worn by a user. In response to the impedance being below a threshold, the method further comprises waking up a processor of the heart rate monitor from a sleep mode. The method further comprises sensing, by the control circuitry, a cardiac electrical activity of the user utilizing the pair of sensors, and calculating, by the processor, a heart rate of the user based on the cardiac electrical activity. The method further comprises determining, by the processor, if the heart rate is within a range of heart rate values. In response to the heart rate being within the range of heart rate values, the method further comprises powering up a plurality of RF transmitters that transmit information utilizing different protocols, and transmitting simultaneously, by the plurality of RF transmitters, the heart rate utilizing the different protocols to at least one external device.

Another embodiment comprises a system that includes a garment wearable by a user and a heart rate monitor. The garment includes snap contact that are each electrically coupled to one of a pair of sensors within the garment. The heart rate monitor includes a pair of contacts that are removably coupled to the snap contacts, a processor, and control circuitry. The control circuitry detects a change in impedance across the contacts, and responsive to the impedance being below a threshold, the control circuitry wakes up the processor from a sleep mode, and senses a cardiac electrical activity of the user utilizing the pair of sensors. The heart rate monitor further includes a first RF transmitter that transmits information using a 5.3 kilohertz (kHz) analog signal protocol, a second RF transmitter that transmits information using Bluetooth Lowe Energy (BLE) protocol, and a third RF transmitter that transmits information using ANT+ protocol. The processor calculates a heart rate of the user based on the cardiac electrical activity, determines if the heart rate is within a range of heart rate values, and in response to the heart rate being within the range of heart rate values, the processor powers up the RF transmitters, and directs the RF transmitters to simultaneously transmit the heart rate information utilizing different protocols to at least one external devices.

The above summary provides a basic understanding of some aspects of the specification. This summary is not an extensive overview of the specification. It is intended to neither identify key or critical elements of the specification nor delineate any scope particular embodiments of the specification, or any scope of the claims. Its sole purpose is to present some concepts of the specification in a simplified form as a prelude to the more detailed description that is presented later.

DESCRIPTION OF THE DRAWINGS

Some embodiments are now described, by way of example only, and with reference to the accompanying drawings. The same reference number represents the same element or the same type of element on all drawings.

DESCRIPTION

The figures and the following description illustrate specific exemplary embodiments. It will thus be appreciated that those skilled in the art will be able to devise various arrangements that, although not explicitly described or shown herein, embody the principles of the embodiments and are included within the scope of the embodiments. Furthermore, any examples described herein are intended to aid in understanding the principles of the embodiments, and are to be construed as being without limitation to such specifically recited examples and conditions. As a result, the inventive concept(s) is not limited to the specific embodiments or examples described below, but by the claims and their equivalents.

Figure 1:
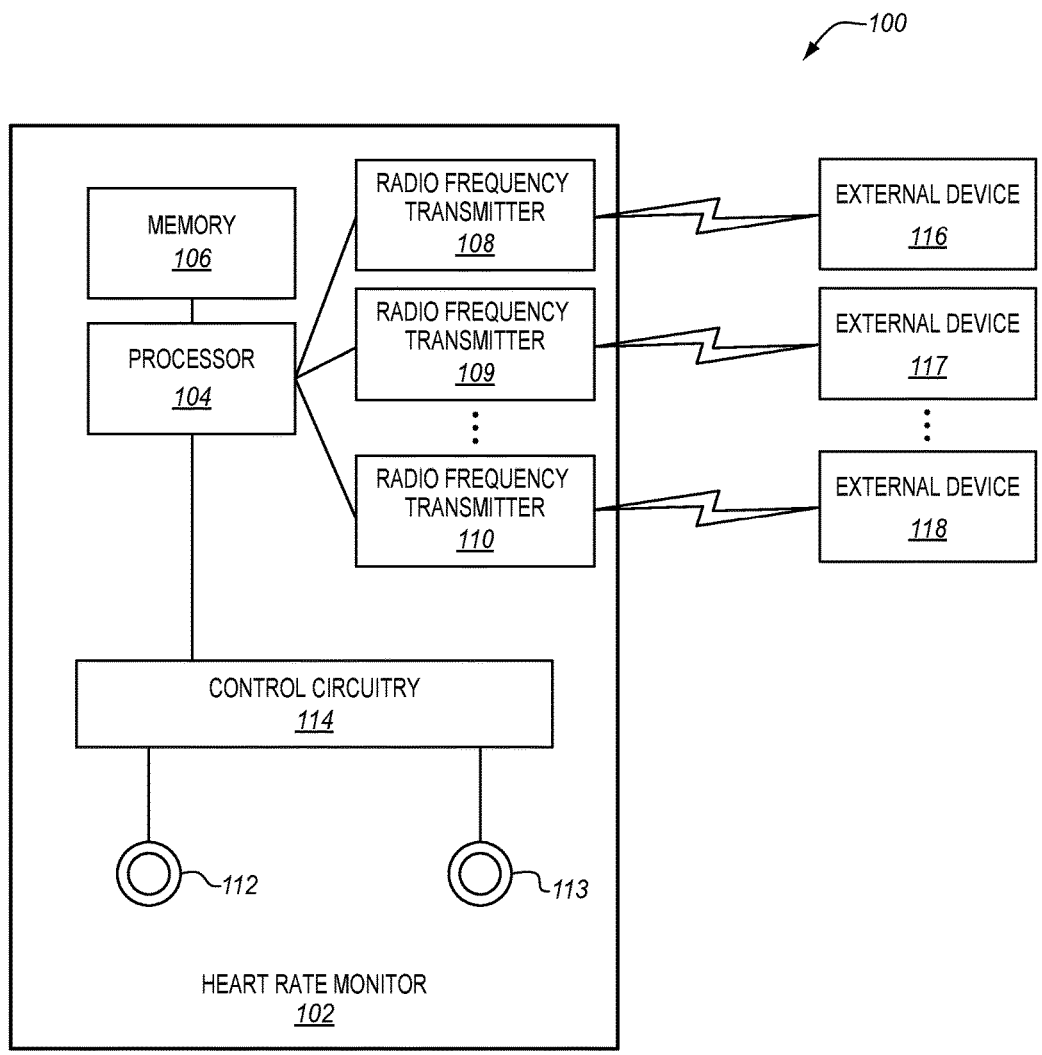
FIG. 1. Illustrates a system that includes a heart monitor in an exemplary embodiment.

FIG. 1 illustrates a system 100 that includes a heart rate monitor 102 in an exemplary embodiment. Monitor 102 is capable of sensing cardiac electrical activity of a user, and providing the heart rate of the user to one or more external devices 116-118. External devices 116-118 may comprise exercise watches, cycling computers, exercise equipment, smart phones, etc. External devices 116-118 receive the heart rate from monitor 102, and display, record, track, upload, etc., the heart rate of the user. For example, if external device 116 comprises a cycling computer, then external device 116 may display the user's heart rate provided by monitor 102 during a bike ride. This type of information allows the user to either train to a particular heart rate zone, or to be made aware of the level of effort expended by the user during the activity on the bicycle.

A number of different wireless protocols are in use by different manufacturers of exercise watches, cycling computers, exercise equipment, etc. One type of wireless protocol used in the fitness industry uses a 5.3 kHz analog signal to transmit the heart rate of a user to equipment, and is widely adopted in exercise equipment found at a gym. This protocol is rudimentary and does not support bi-directional communication with equipment. Thus, it is not possible for heart rate monitoring devices to determine if an 5.3 kHz endpoint device exists that supports this protocol.

Another type of wireless protocol used in the fitness industry uses is BLE, which operates in the 2.4 GHz Industrial, Scientific, and Medical (ISM) band and is a packet-based protocol with a master-slave structure. BLE devices are paired together before they communicate. BLE requires acknowledgment (ACK) messages, which allows a BLE transmitter to determine if a BLE endpoint device exists when the BLE endpoint device returns an ACK message to the transmitter. Typical BLE devices include smartphones, although BLE is slowly being adopted by fitness equipment manufacturers.

Another type of wireless protocol used in the fitness industry is ANT+. ANT+ is a subset of the ANT protocol, which also operates in the 2.4 GHz ISM band. ANT+ is another packet-based protocol with a master-slave structure, although ANT+ devices can switch between master mode and slave mode to route traffic to other ANT+ devices. ANT+ is designed for the interoperable collection and transfer of sensor data. ANT+ devices are also paired together before they communicate. ANT+ also supports ACK messages, which allows an ANT+ transmitter to determine if an ANT+ endpoint devices exists when the ANT+ endpoint device returns an ACK message to the transmitter. The ANT+ protocol does not require ACK messages, but they may be implemented if desired. However, the future of the ANT+ protocol may require ACK messages, similar to BLE. ANT+ in the fitness space is currently more widely implemented than BLE, and a number of ANT+ capable sensors are available today. For example, in the cycling world, ANT+ is used for cadence sensors, cycling computers, speed sensors, power meters, etc.

One problem in the fitness space is that typical heart rate transmitters only work with receiving devices that support the same wireless interfaces. For example, if a user purchased a heart rate transmitter and strap that only used the analog 5.3 kHz interface, then it would only be able to communicate with receiving devices that supported the analog 5.3 kHz interface. If the user wanted to monitor or track their heart rate using a device that did not support 5.3 kHz, then they would be unable to do so. The same problem also applies to BLE and ANT+ heart rate monitors. In a worse case scenario, the user may have a heart rate monitor that supports one of the 5.3 kHz, BLE, or ANT+ interfaces, which may not be able to provide the heart rate of the user to their smart watch, exercise equipment, cycling computer, smart phone, etc. This problem of interoperability between the different wireless protocols in use today generates a lot of confusion for the consumer regarding whether their equipment and devices will be able to communicate with their heart rate monitor. For example, if the user purchases a 5.3 kHz heart rate monitor, an ANT+ watch, and a BLE stationary bike, neither the watch nor the stationary bike would be able to display the heart rate of the user.

The embodiments described herein solve these and other problems by transmitting the heart rate of a user utilizing multiple wireless interfaces that can communicate with a wide variety of RF endpoints. This allows a user to purchase and use one heart rate monitor that can operate with a large number of fitness devices without worrying about whether the wireless interface of the heart rate monitor is compatible with their equipment. Also, the embodiments described herein may utilize multiple RF transmitters to simultaneously transmit the heart rate of the user to multiple devices. For example, the heart rate of the user may be provided to a piece of exercise equipment using the 5.3 kHz protocol concurrently with a smart phone using the BLE protocol. This type of functionality may be desirable as it allows the user's heart rate to be displayed in real-time on the exercise equipment while being recorded or logged by the user's smart phone.

While the specific hardware implementation of monitor 102 is subject to design choices, one particular embodiment may include one or more processors 104 communicatively coupled with a memory 106. Processor 104 includes any electronic circuits and/or optical circuits that are able to perform functions. For example, processor 104 may perform any functionality described herein for monitor 102. Processor 104 may include one or more Central Processing Units (CPU), microprocessors, Digital Signal Processors (DSPs), Application-specific Integrated Circuits (ASICs), Programmable Logic Devices (PLD), control circuitry, etc. Some examples of processors include INTEL® CORE™ processors, Advanced Reduced Instruction Set Computing (RISC) Machines (ARM®) processors, etc.

Memory 106 includes any electronic circuits, and/or optical circuits, and/or magnetic circuits that are able to store data. For instance, memory 106 may be used to store programmed instructions that are executed by processor 104 to perform any of the functions described herein for monitor 102, may be used to store samples or records of a user's heart rate over time for subsequent transfer to another device, etc. Memory 106 may include one or more volatile or non-volatile Dynamic Random Access Memory (DRAM) devices, FLASH devices, volatile or non-volatile Static RAM devices, magnetic disk drives, Solid State Disks (SSDs), etc. Some examples of non-volatile DRAM and SRAM include battery-backed DRAM and battery-backed SRAM.

In this embodiment, monitor 102 includes a plurality of RF transmitters 108-110. RF transmitters 108-110 utilize different wireless interfaces and/or protocols to communicate with external devices 116-118. For example, RF transmitters 108-110 may include 5.3 kHz protocol transmitters, BLE protocol transmitters, and/or ANT+ protocol transmitters, each of which has been previously described. Although only three RF transmitters are shown, monitor 102 may include any number of RF transmitters as a matter of design choice. Further, multiple RF transmitters may support the same protocol, thereby allowing monitor 102 to communicate with a plurality of external devices 116-118 using a point-to-point protocol, such as BLE or ANT+. In this embodiment, RF transmitters 108-110 comprise any component, system, or device that is able to transmit an RF signal that conveys information regarding the heart rate of a user to one or more external devices 116-118.

In this embodiment, monitor 102 further includes control circuitry 114, which is electrically coupled to a pair of contacts 112-113. Control circuitry 114 comprises any component, system, or device that is able to perform measurements on contacts 112-113, and to provide information to processor 104. For instance, when contacts 112-113 are electrically connected to a heart rate sensing strap or a heart rate sensing garment, control circuitry 114 is able to measure and amplify the cardiac electrical output of a user's heart, and to provide this information to processor 104. Contacts 112-113 may include snaps or other features that allows monitor 102 to be removed from a garment or strap to allow the garment or strap to be cleaned or washed.

Figure 2:
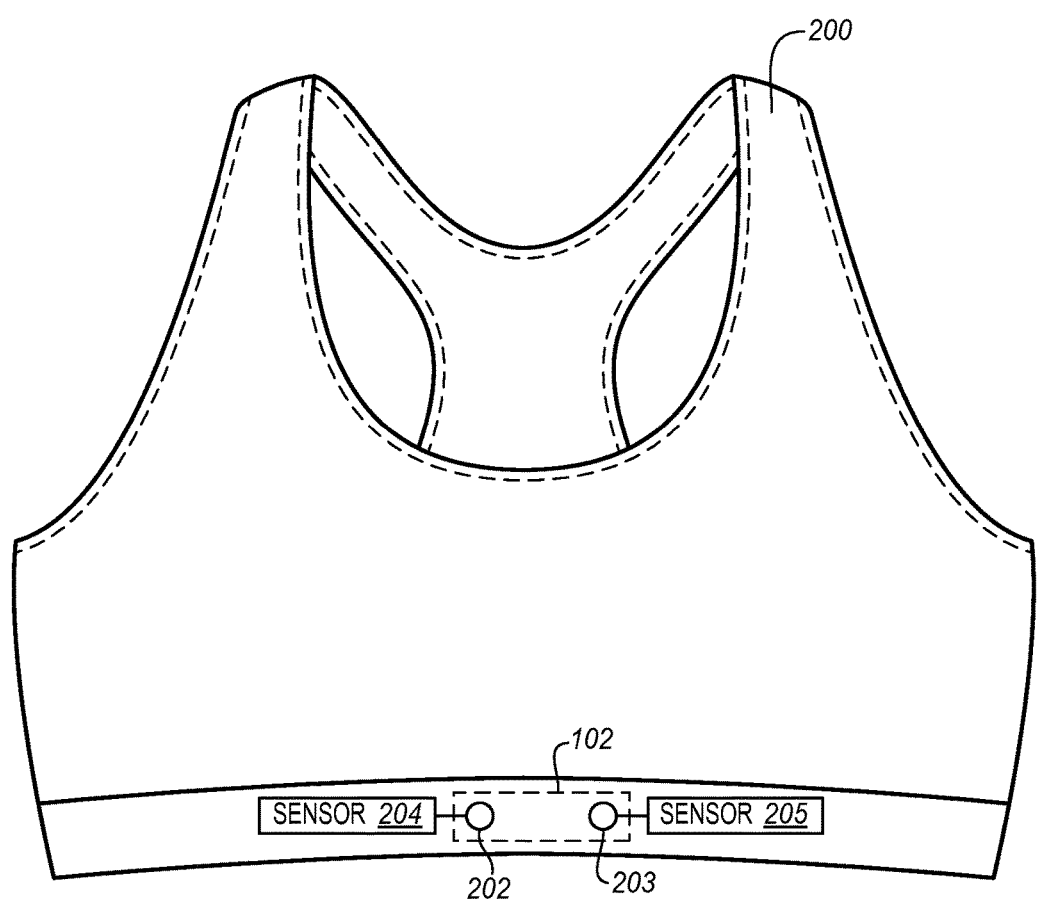
FIG. 2 illustrates the system of FIG. 1 in another exemplary embodiment.

FIG. 2 illustrates system 100 in another exemplary embodiment. In this embodiment, system 100 further includes a garment 200. Garment 200 is wearable by a user, and resembles a tank top in FIG. 2. Garment includes a pair of snaps 202-203 that enable monitor 102 to be removably coupled to garment 200 via contacts 112-113. For example, contact 112 of monitor 102 may removably mate with snap 202 on garment 200, and contact 113 of monitor 102 may removably mate with snap 203 on garment 200. In this embodiment, garment 200 further includes sensor 204-205, which contact the skin of the user when wearing garment 200. Sensors 204-205 comprise any component, system, or device that is able to sense the cardiac electrical activity of the user, and to provide this cardiac electrical activity to snaps 202-203, respectively. When monitor 102 is mounted to garment 200 and the user is wearing garment 200 (e.g., contacts 112-113 are mated with snaps 202-203, respectively, and sensors 204-205 of garment 200 are in contact with the skin of the user), the cardiac electrical activity of the user is sensed by sensors 204-204 and relayed to control circuitry 114 of monitor 102 and subsequently, to processor 104 of monitor 102.

Although garment 200 is illustrated in FIG. 2 as a sports bra for purposes of discussion, one skilled in the art will recognize that garment 200 may comprise any type of wearable item that includes sensors 204-205 and snaps 202-203.

Figure 3:
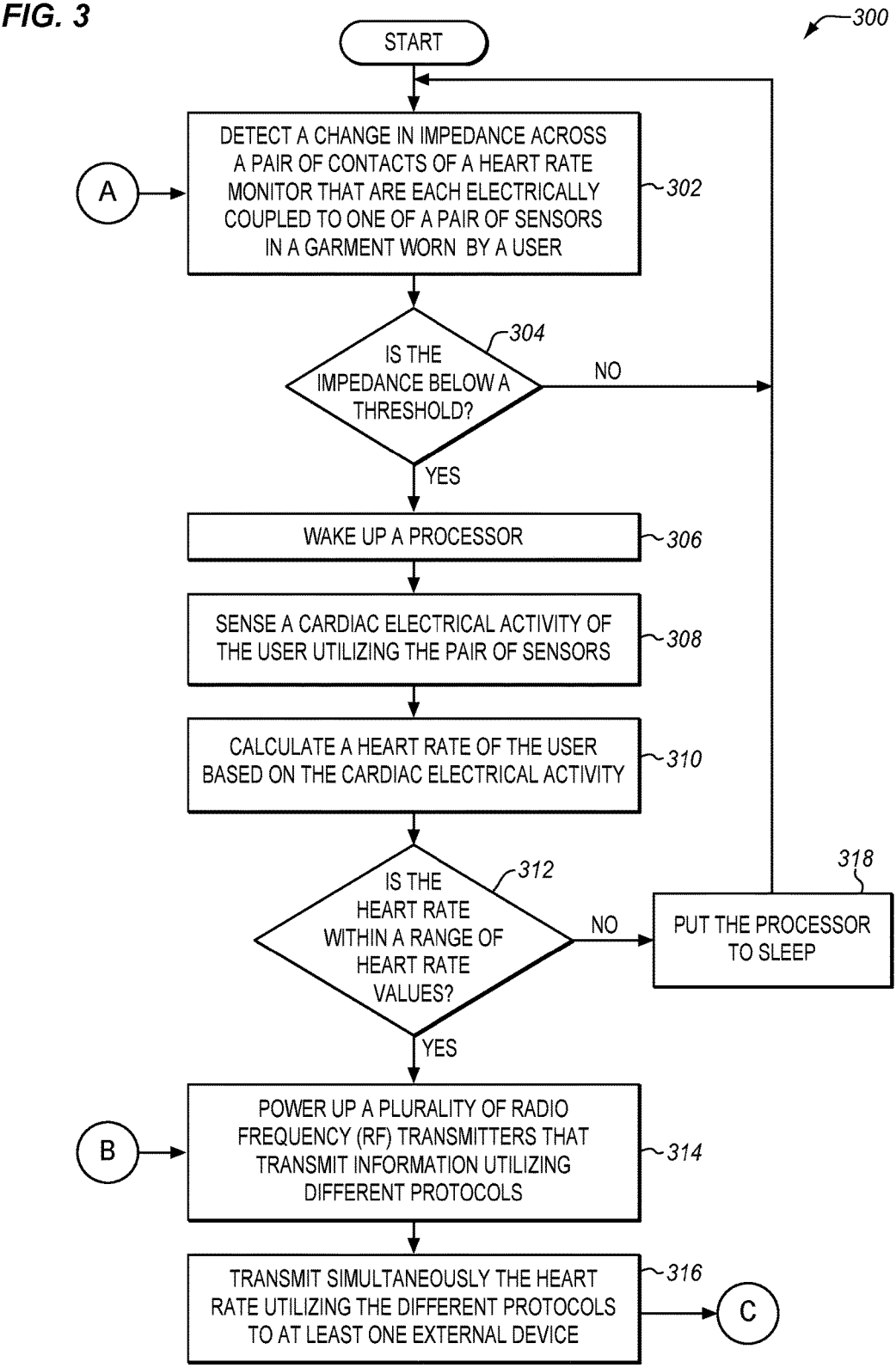
FIGS. 3-4 are flow charts of a method of monitoring a user's heart rate in various exemplary embodiments.
Figure 4:
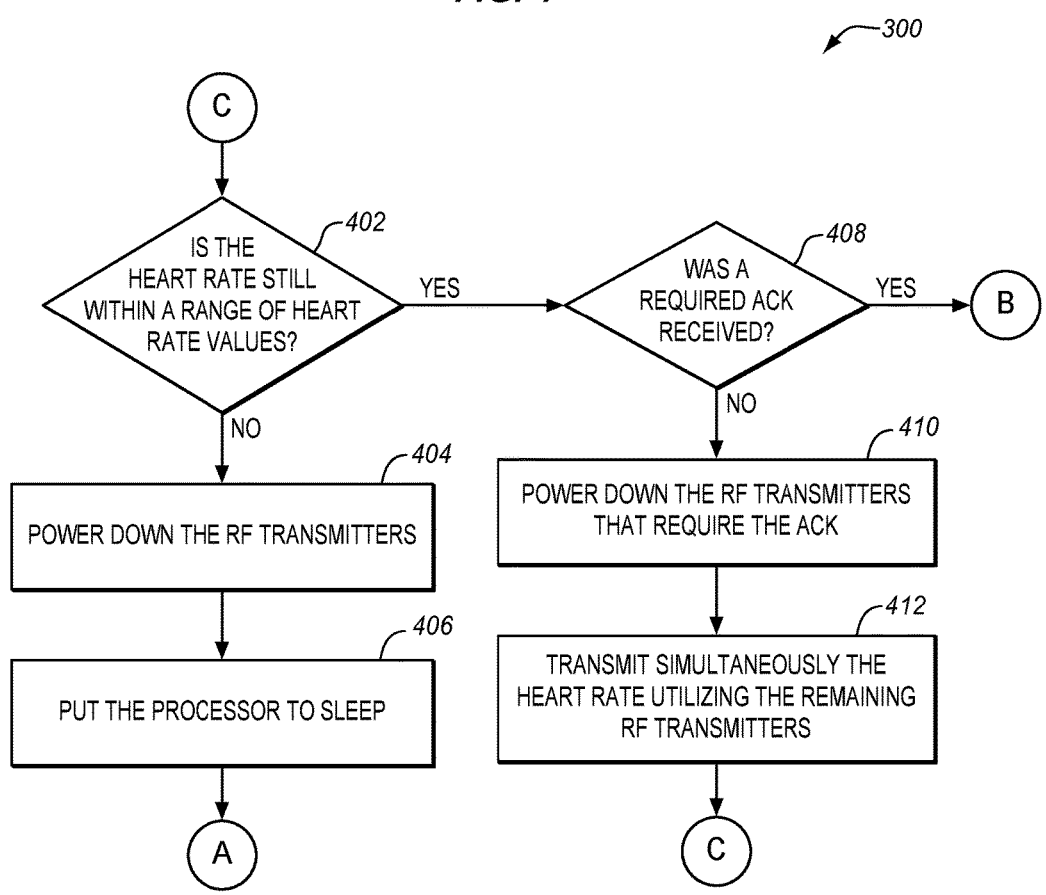

Consider that a user is wearing garment 200 and that monitor 102 is affixed to garment via snaps 202-203. FIGS. 3-4 are flow charts of a method 300 of monitoring a user's heart rate in various exemplary embodiments. Method 300 will be discussed with respect to system 100, although one skilled in the art will recognize that method 300 may be performed by other systems, not shown. Further the steps of method 300 are not all inclusive, and method 300 may include other steps not shown. The steps may also be performed in an alternate order.

Control circuitry 114 monitors the impedance across contacts 112-113, which are electrically coupled to sensors 204-205 in garment 200. In response to the user wearing garment 200, sensors 204-205 contact the skin of the user, and the impedance is reduced from an open circuit condition to a lower value. Control circuitry 114 detects the change in the impedance (see step 302 of method 300). Control circuitry 114 determines if the impedance is below a threshold (see step 304). If the impedance is not below the threshold, then control circuitry 114 continues to monitor the impedance (see step 302). For instance, the user may be wearing garment 200, but sensors 204-205 are only imperfectly electrically coupled to the user. Typically, a user will wet the skin-side of garment 200 proximate to sensors 204-205, to ensure that a sufficient electrical conductivity is present between the skin of the user and sensors 204-205. If the impedance is below the threshold, then control circuitry 114 wakes up processor 104 from a sleep mode (see step 306). Processor 104 may be placed in the sleep mode to save electrical power when the user is not wearing garment 200 with monitor 102 in place. Waking up processor 104 from a sleep mode may entail a signaling change on a pin of processor 104, which generates a wake-up signal for processor 104, or the application of electrical power to processor 104 using a signaling change on a power supply from control circuitry 114.

Control circuitry 114 senses the cardiac electrical activity of the user via sensors 204-205 (see step 308). This cardiac electrical activity is around 1 millivolt of differential voltage across sensors 204-205, which is amplified and may be filtered by control circuitry 114. Control circuitry 114 then provides the cardiac electrical signal to processor 104. This signal may be provided as a digital pulse train to processor 104, which then is able to infer the heart rate of the user based on the periodicity of the pulse train. This signal may also be provided as a differential or single-ended analog signal to processor 104, which then is able to sample the analog signal to infer the heart rate of the user based on the periodicity of the analog signal. However, these are merely two possible examples of how control circuitry 114 may provide the cardiac electrical signal to processor 104, and others exist as a matter of design choice.

Processor 104 utilizes the cardiac electrical signal provided by control circuitry 114 to calculate a heart rate of the user (see step 310). For instance, processor 104 may determine a number of digital pulses during a time period, which can be used to calculate the heart rate of the user in typical format (e.g., beats per minute). Processor 104 then determines if the heart rate of the user is within a range of heart rate values (see step 312). For example, it may be desirable that the heart rate signal sensed by garment 200 is within a valid range of heart rates for a user (e.g., 30 to 200 beats per minute). This step may be used to ensure that sensors 204-205 are indeed capturing electrical signals from the user's heart rather than electrical noise generated by a nearby RF or electromagnetic radiator. If the heart rate is not within the range of heart rate values, then processor 104 is put to sleep in an optional step of method 300 (see step 318). In this case, putting processor 104 to sleep may entail a sleep mode in the operation of processor 104, turning off an electrical power supply for processor 104, etc.

If the heart rate is within the range of heart rate values, then processor 104 powers up RF transmitters 108-110 (see step 314). Powering up RF transmitters 108-110 may be performed in a number of different ways as a matter of design choice. For instance, RF transmitters 108-110 may support a sleep mode, which is a reduced power state for RF transmitters 108-110. In addition or instead of, an electrical power supply for RF transmitters 108-110 may be turned on, thereby supplying electrical power to RF transmitters 108-110. Powering up RF transmitters 108-110 places RF transmitters 108-110 in an active RF state, ready to transmit.

Processor 104 directs RF transmitters 108-110 to transmit the heart rate of the user simultaneously to one or more external devices 116-118 (see step 316). In this embodiment, each of RF transmitters 108-110 utilizes a different protocol to transmit the heart rate of the user to external devices 116-118. For instance, RF transmitter 108 may utilize the 5.3 kHz protocol, RF transmitter 109 may utilize the BLE protocol, and RF transmitter 110 may utilize the ANT+ protocol. External devices 116-118 receive the heart rate of the user, and display, log, upload, etc., this information. For example, a user's smart phone may receive the heart rate of the user over the BLE protocol, and upload this information to strava to allow the user to review the heart rate after exercise. Simultaneously, the gym equipment the user is exercising on receives the user's heart rate over the 5.3 kHz protocol, which is displayed to the user during the exercise.

In some embodiments, processor 104 may re-check to determine if the heart rate of the user is within the range of heart rate values (see step 402 of FIG. 4). For instance, if the user removes garment 200 or an imperfect electrical contact between the skin of the user and sensors 204-205 prevents control circuitry 114 from receiving a cardiac electrical output from the user, then processor 104 powers down RF transmitters 108-110 (see optional step 404) and processor 104 is placed into a sleep mode (see optional step 406). At this point the performance of method 300 returns to step 302. However, if the heart rate of the user is still within the range of heart rate values, processor 104 determines if an ACK message was received from one or more of external devices 116-118 (see optional step 408). In some cases, a protocol in use by RF transmitters 108-110 may require an ACK message (e.g., BLE or possibly, ANT+). If a required ACK message is not received, then it is likely that none of external devices 116-118 support the protocol requiring the ACK message. In this case, processor 104 can reduce a power consumption of monitor 102 by powering down RF transmitters 108-110 that are using the protocol requiring the ACK message (see optional step 410). For instance, if RF transmitter 109 utilizes the BLE protocol and a BLE ACK message required by the protocol was not received from one or more of external devices 116-118, then processor 104 powers down RF transmitter 109. If RF transmitter 110 utilizes the ANT+ protocol and an ANT+ ACK message that may be required by the protocol was not received from one or more external devices 116-118, then processor 104 powers down RF transmitter 110. The remaining RF transmitters (e.g., RF transmitter 108) continue to transmit the heart rate of the user to one or more external devices 116-118 (see optional step 412). Processing of method 300 then returns to step 402.

In some embodiments, processor 104 may power down RF transmitters 108-110 in response to one or more of the RF transmitters 108-110 receiving an ACK message. For example, if RF transmitter 109 receives a BLE or ANT+ ACK message, then processor 104 may power down other RF transmitter 108 to save power, with the idea being that providing the 5.3 kHz heart rate signal may be redundant, since the external device in use by the user already supports one or more protocols that support ACK messages.

In some embodiments, processor 104 may capture the heart rate of the user over time and store or record the heart rate of the user in memory 106. This process may occur when monitor 102 is not in communication with external devices 116-118 that are capable of recording or logging the user's heart rate. For example, if a BLE or ANT+RF endpoint is not detected, then processor 104 may store the user's heart rate over time in a record in memory 106. When at a later time when external devices 116-118 is detected that is capable of receiving the record, then processor 104 may transfer the record from memory 106 to one or more of external devices 116-118. For instance, consider a swimmer in the water that is wearing monitor 102. Typically, the water will attenuate a 2.4 GHz transmission to the extent that even if the swimmer were to have a BLE or ANT+ capable smart phone on their person while swimming, it may be unlikely that the smart phone would be able to receive a BLE or ANT+ transmission from monitor 102. In this case, monitor 102 may record the user's heart rate over time, and upon connecting with the smart phone after the swimmer has left the water (e.g., via BLE or ANT+), monitor 102 transfers the log or record of the user's heart rate to the user's smart phone. In some cases, processor 104 may generate and store timestamps along with the user's heart rate in memory 106. This may occur if monitor 102 has access to a time source. For instance, processor 104 may implement a software-based clock, or monitor 102 may include a Real Time Clock (RTC) source (e.g, as a separate circuit or integrated circuit within processor 104). The use of correlating the user's stored heart rate with timestamps allows the user to identify their heart rate at different times during the activity.

In some embodiments, external devices 116-118 may include other non-fitness related devices that are capable of receiving the heart rate of the user from monitor 102. For example, a BLE and/or ANT+ enabled gateway may receive the heart rate of the user from monitor 102, and utilize an wired (e.g., Ethernet) and/or a wireless (e.g., 802.11 Wi-Fi) network to provide the heart rate of the user to an external display. This may be desirable in a group fitness environment when the heart rates of each of a group of people is being displayed by the external monitor during the fitness routine. In other embodiments, the BLE and/or ANT+ enabled gateway may receive the heart rate of the user from monitor 102, and utilize the wired and/or the wireless network to forward the heart rate to a website, a cloud-based fitness application and/or service, etc. In other embodiments, monitor 102 may provide the heart rate of the user to an external display directly that supports BLE and/or ANT+ (e.g., a large-format display in a fitness class) utilizing one or more of RF transmitters 108-110. In any of the embodiments, the use of multiple RF transmitters 108-110 allows monitor 102 to provide the user's heart rate to multiple external devices 116-118 simultaneously.

The use of a multi-protocol approach outlined above for providing the user's heart rate to various external devices 116-118 (e.g., cycling computers, exercise equipment, smart phones, exercise watches, etc.) removes the guesswork out of interoperability between RF endpoints that may support different protocols for the reception of the user's heart rate. This simplifies the user's experience and further enables multiple external devices 116-118 to receive the user's heart rate information simultaneously, as described previously with respect to a user's smart phone and a piece of gym equipment. This simultaneous reception option may be desirable in group fitness events where the user's heart rate is displayed on a piece of gym equipment that is in use by the user along with displaying the user's heart rate on a group display device for the event.

Any of the various elements shown in the figures or described herein may be implemented as hardware, software, firmware, or some combination of these. For example, an element may be implemented as dedicated hardware. Dedicated hardware elements may be referred to as "processors", "controllers", or some similar terminology. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), logic, or some other physical hardware component.

Also, an element may be implemented as instructions executable by a processor or a computer to perform the functions of the element. Some examples of instructions are software, program code, and firmware. The instructions are operational when executed by the processor to direct the processor to perform the functions of the element. The instructions may be stored on storage devices that are readable by the processor. Some examples of the storage devices are digital or solid-state memories, magnetic storage media such as a magnetic disks and magnetic tapes, hard drives, or optically readable digital data storage media.

Although specific embodiments were described herein, the scope is not limited to those specific embodiments. Rather, the scope is defined by the following claims and any equivalents thereof.

The invention claimed is:

1. A heart rate monitor, comprising:
a pair of contacts that are each configured to electrically couple to one of a pair of sensors in a garment worn by a user;
a processor;
control circuitry that is configured to detect a change in impedance across the pair of contacts, and responsive to determining that the impedance is below a threshold, the control circuitry is configured to wake up the processor from a sleep mode, and to sense a cardiac electrical activity of the user utilizing the pair of sensors; and
a plurality of Radio Frequency (RF) transmitters that are configured to transmit information utilizing different protocols,
wherein the processor is configured to calculate a heart rate of the user based on the cardiac electrical activity, and responsive to determining that the heart rate is within a range of heart rate values, the processor is configured to power up the RF transmitters, and to direct the RF transmitters to simultaneously transmit the heart rate utilizing the different protocols to at least one external device.

2. The heart rate monitor of claim 1, wherein:
the processor is configured, responsive to determining that the heart rate is outside of the range of heart rate values, to power down the RF transmitters, and to enter the sleep mode.

3. The heart rate monitor of claim 1, wherein:
the processor is configured to power down the RF transmitters that are transmitting the heart rate utilizing one of the different protocols responsive to determining that an acknowledgment (ACK) response required by the one of the different protocols has not been received from the at least one external device.

4. The heart rate monitor of claim 1, wherein:
the processor is configured to power down the RF transmitters that are not transmitting the heart rate utilizing one of the different protocols responsive to determining that an acknowledgment (ACK) response has been received from the at least one external device for the one of the different protocols.

5. The heart rate monitor of claim 1, further comprising:
the garment worn by the user.

6. The heart rate monitor of claim 5, wherein:
the garment comprises one of a sports bra, a tank top, and a bra.

7. The heart rate monitor of claim 1, wherein:
at least one of the RF transmitters utilizes a 5.3 kilohertz (kHz) analog signal as one of the different protocols.

8. The heart rate monitor of claim 7, wherein:
at least one of the RF transmitters utilizes Bluetooth Low Energy (BLE) as one of the different protocols.

9. The heart rate monitor of claim 8, wherein:
at least one of the RF transmitters utilizes ANT+ as one of the different protocols.

10. The heart rate monitor of claim 1, further comprising:
a memory,
wherein the processor is configured to store a record of the heart rate over time in the memory, to identify one of the at least one external device that is capable of receiving the record, and to transfer the record to the identified external device utilizing at least one of the RF transmitters.

11. A method operable by a heart rate monitor, the method comprising:
detecting, by control circuitry of the heart rate monitor, a change in impedance across a pair of contacts of the heart rate monitor that are each electrically coupled to one of a pair of sensors in a garment worn by a user;
waking up a processor of the heart rate monitor from a sleep mode responsive to determining that the impedance is below a threshold;
sensing, by the control circuitry, a cardiac electrical activity of the user utilizing the pair of sensors;
calculating, by the processor, a heart rate of the user based on the cardiac electrical activity;
powering up, by the processor, a plurality of Radio Frequency (RF) transmitters that transmit information utilizing different protocols responsive to determining that the heart rate is within a range of heart rate values; and
transmitting simultaneously, by the plurality of RF transmitters, the heart rate utilizing the different protocols to at least one external device.

12. The method of claim 11, further comprising:
responsive to determining that the heart rate is outside of the range of heart rate values, powering down the RF transmitters; and
entering, by the processor, the sleep mode.

13. The method of claim 11, further comprising:
powering down the RF transmitters that are transmitting the heart rate utilizing one of the different protocols responsive to determining that an acknowledgment (ACK) response required by the one of the different protocols has not been received from the at least one external device.

14. The method of claim 11, further comprising:
powering down the RF transmitters that are not transmitting the heart rate utilizing one of the different protocols responsive to determining that an acknowledgment (ACK) response has been received from the at least one external device for the one of the different protocols.

15. The method of claim 11, wherein transmitting further comprises:
transmitting the heart rate to the at least one external device utilizing a 5.3 kilohertz (kHz) analog signal as one of the different protocols.

16. The method of claim 15, wherein transmitting further comprises:
transmitting the heart rate to the at least one external device utilizing Bluetooth Low Energy (BLE) as one of the different protocols.

17. The method of claim 16, wherein transmitting further comprises:
transmitting the heart rate to the at least one external device utilizing ANT+ as one of the different protocols.

18. The method of claim 11 further comprising:
storing a record of the heart rate over time in a memory;
identifying one of the at least one external device that is capable of receiving the record; and
transferring the record to the identified external device utilizing at least one of the RF transmitters.

19. A system, comprising:
a garment wearable by a user that includes snap contacts and a pair of sensors, wherein the snap contacts are each electrically coupled to one of the pair of sensors;
a heart rate monitor comprising:
a pair of contacts that are removably coupled to the snap contacts;
a processor;
control circuitry that is configured to detect a change in impedance across the pair of contacts, and responsive to the impedance being below a threshold, the control circuitry configured to wake up the processor from a sleep mode, and to sense a cardiac electrical activity of the user utilizing the pair of sensors; and
a first Radio Frequency (RF) transmitter that is configured to transmit information utilizing a 5.3 kilohertz (kHz) analog signal protocol;
a second RF transmitter that is configured to transmit information utilizing Bluetooth Low Energy (BLE) protocol; and
a third RF transmitter that is configured to transmit information utilizing ANT+ protocol,
the processor configured to calculate a heart rate of the user based on the cardiac electrical activity, and responsive to determining that the heart rate is within a range of heart rate values, the processor is configured to power up to the RF transmitters, and to direct the RF transmitters to simultaneously transmit the heart rate utilizing different protocols to at least one external device.

20. The system of claim 19, wherein:
the processor is configured, responsive to determining that the heart rate is outside of the range of heart rate values, to power down the RF transmitters, and to enter the sleep mode.

21. The system of claim 19, wherein the heart rate monitor further comprises:
a memory,
wherein the processor is configured to store a record of the heart rate over time in the memory, to identify one of the at least one external device that is capable of receiving the record,
and to transfer the record to the identified external device utilizing at least one of the RF transmitters.

22. The system of claim 19, wherein:
the processor is configured to power down the second RF transmitter responsive to determining that a BLE acknowledgment (ACK) response has not been received from the at least one external device.

23. The system of claim 19, wherein:
the processor is configured to power down the third RF transmitter responsive to determining that an ANT+ acknowledgment (ACK) response has not been received from the at least one external device.

* * * * *